United States Patent
Wang et al.

(10) Patent No.: US 7,838,264 B2
(45) Date of Patent: Nov. 23, 2010

(54) **METHOD FOR PRODUCING ANTCIN K, ZHANKUIC ACID A, ZHANKUIC ACID B OR ZHANKUIC ACID C FROM THE MYCELIUM OF *ANTRODIA CINNAMOMEA***

(75) Inventors: Yu-Lung Wang, Taipei (TW); Shu-Chun Chung, Taipei (TW)

(73) Assignee: Cojet Biotech Inc., Taipei (TW)

( * ) Notice: Subject to any disclaimer, the term of this patent is extended or adjusted under 35 U.S.C. 154(b) by 70 days.

(21) Appl. No.: 12/141,656

(22) Filed: Jun. 18, 2008

(65) Prior Publication Data

US 2009/0227001 A1 Sep. 10, 2009

(30) Foreign Application Priority Data

Mar. 4, 2008 (TW) .............................. 97107406 A (51) Int. Cl.
*C12P 35/02* (2006.01)
(52) U.S. Cl. .................. 435/52; 435/243; 435/254.1
(58) Field of Classification Search .................. 435/52, 435/243, 254.1
See application file for complete search history.

(56) References Cited

U.S. PATENT DOCUMENTS 5,116,494 A * 5/1992 Chick et al. ................. 210/192
6,558,943 B1 * 5/2003 Li et al. .................... 435/254.1

OTHER PUBLICATIONS

Yano et al. Agric. Biol. Chem. (1991) 55(2): 379-385.*
Chang et al. Bot. Bull. Acad. Sin. (2005) 46: 151-154, downloaded from http://ejournal.cinica.edu.tw.bbas/content/2005/2/Bot462-08.html on Mar. 9, 2010, 7 pages.*
Chang et al. J. Food Drug Anal. (2006) 14(2) 174-182.*
Shih et al. Process Biochem. (2006) 41: 1129-1135.*
Lu et al. Life Sci. (2006) 79: 252-258.*
Geethangili et al. "Review of Pharmacalogical Effects of *Antrodia camphorata* and its Bioactive Compounds" eCAM (2009) 15 pages published by Oxford University Press.*
Chen et al. "New Steroid Acids from *Antrodia cinnamomea*—a Fungal Parsite of *Cinnamoum micranthum*" J. Nat. Prod. (1995) 58: 1655-1661.*

* cited by examiner

*Primary Examiner*—Sandra Saucier
*Assistant Examiner*—Susan Hanley
(74) *Attorney, Agent, or Firm*—WPAT, P.C.; Anthony King (57) ABSTRACT

The present invention provides a method for producing antcin K, zhankuic acid A, zhankuic acid B or zhankuic acid C from the mycelium of the fungus *Antrodia cinnamomea* by culturing the fungus on a gel medium, harvesting the mycelium and isolating the products by HPLC.

14 Claims, 7 Drawing Sheets

Group 1- mock, 100x.

Group 4 – low dose, 100x.

Group 2 – negative control, 100x.

Group 5 – moderate dose, 100x.

Group 3 – positive control, 100x.

Group 6 – high dose, 100x.

Figure 7

METHOD FOR PRODUCING ANTCIN K, ZHANKUIC ACID A, ZHANKUIC ACID B OR ZHANKUIC ACID C FROM THE MYCELIUM OF *ANTRODIA CINNAMOMEA*

This application claims priority to Taiwanese Application No. 097107406, filed Mar. 4, 2008.

FIELD OF THE INVENTION

The present invention provides a composition of *Antrodia cinnamomea*, a mixture of *Antrodia cinnamomea*, a fungal mixture and preparation thereof. In particular, the present invention can massively produce fungi in gel mediums.

BACKGROUND OF THE INVENTION

*Antrodia cinnamomea* is a perennial fungus under the classification of Aphyllophorales, Polyporaceae, and *Antrodia*. It is an unique Taiwanese fungus only grown on Taiwanese *Cinnamomum kanehirae* Hay. *Antrodia cinnamomea* is a special and precious medicinal fungus as well as the most expensive wild fungus nowadays in Taiwan. The first publication of *Antrodia cinnamomea* is in 1990, when Zhang and Su presented *Antrodia cinnamomea* fruiting body with contaminated *Ganoderma* spores and grouped it as a new species under *Ganoderma commmphoratum* Zang & Su. In 1995, the second new species reported by Chang and Chou based on morphology and cultivation features of *Antrodia cinnamomea*. Particularly, they discovered that *Antrodia cinnamomea* is wood brown rot fungus, and classified it as a new species *Antrodia cinnamomea* Chang T T & W N Chou under *Antrodia*. In 1997, the third new species publication renamed this species as *Antrodia cinnamomea* by Wu. In 2004, based on ICBN Article 9. 12 (Greuter et al., 2000), Chang and Chou disregarded the misleading *Ganoderma comphoratum* and *Antrodia camphorate*, and recovered to *Antrodia cinnamomea*.

Research has shown that the extract from *Antrodia cinnamomea* fruiting body contains three triterpene compounds which are antcin A, antcin B and antcin C. Three new triterpene compounds has been identified in further research as antrocin, 4,7-dimethoxy-5-methyl-1,3-benzodioxole, and 2,2',5,5'-tetramethoxy-3,4,3',4'-bimethyl-enedioxy-6,6'-dimethylbiphenyl. In 1996, another four new triterpene compounds have been found such as antcin E, antcin F, methylantcinate G, and methylanticinate H. In 1996, two ergostane based new compounds were identified from fruiting body extract, such as zhankuic acid D and zhankuic acid E; and three lanostane based new compounds were identified from fruiting body extract as 15α-acetyl-dehydro-sulphurenic acid, dehydroeburicoic acid, and dehydro-sulphurenic acid.

Based on previous research, it is known that *Antrodia cinnamomea* contains complex compounds. Besides triterpene, it contains lots of physiological active substances such as polysaccharides, SOD, adenosine, small molecular protein, vitamin, trace elements, nucleic acid, steroid, blood pressure stabilizing substance, and etc. Previous research revealed that *Antrodia cinnamomea* contains unique triterpene compounds, although their activity of anti-cancer cell growth and neuron cell growth activation is not fully discovered yet.

Because wild *Antrodia cinnamomea* grows in dark, damp, low temperature condition of middle altitude mountainous regions accompanied with its long growth period (over one year), the time to produce fruiting body is very long. *Cinnamomum kanehirae* Hay. and wild *Antrodia cinnamomea* are reserved plants, and current artificial cultivation method is not able to provide mass cultivation and biological activity simultaneously. Besides, serious stealing issue of wild *Antrodia cinnamomea* brings this species the crisis of extinction. Currently, there are three cultivation methods: liquid fermentation, solid cultivation and wood cultivation. Liquid fermentation is used in early stage mainly in industry and academia which is good for mass production with short cultivation time, high yield, and high carbohydrate content in general. However, this method can not produce the effective triterpene compounds. Therefore, the research is restricted to the function of polysaccharide and its potential is limited. Solid cultivation is filling various grains into plastic bag or container as medium for higher yield. It produces some kinds of triterpene with more complete features than that from liquid fermentation. However, the production rate is not stable, and it is hard to separate fungi from its medium. Therefore, the grain medium is usually harvested simultaneously causing less than 5% recovery of *Antrodia cinnamomea*. As a result, total activity is decreasing, and the cultivation time is as long as 3~4 months. Wood cultivation is using *Cinnamomum kanehirae* Hay. to culture *Antrodia cinnamomea*, which is used to solve the stealing problem of *Cinnamomum kanehirae* and *Antrodia cinnamomea* without real benefit. The problems with wood cultivation includes 1~2 years of growth period, limited source of wood, and extreme quality variation between each lot leading to unstable product quality. Due to current shortcoming and limitation of *Antrodia cinnamomea* cultivation, the present invention is applying gel medium to cultivate *Antrodia cinnamomea* in corporation with screening platform to obtain *Antrodia cinnamomea* with cancer cell growth inhibition, liver protection and other activities through medium modification. The advantage of the present invention is not only eliminating the medium effect on its function and higher fungal purity, shortening cultivation time (1~1.5 month), and reducing the contamination chances during long cultivation time, but also improving space circulation for improving unit production rate, and lowering cost.

SUMMARY OF THE INVENTION

The present invention provides a composition of *Antrodia cinnamomea*, a mixture of *Antrodia cinnamomea*, a fungal mixture and preparation thereof. In particular, the present invention can massively produce fungi in gel mediums.

DETAILED DESCRIPTION OF THE INVENTION

Currently, there are three cultivation methods: liquid fermentation, solid cultivation and wood cultivation. Liquid fer- mentation is used in early stage mainly in industry and academia which is good for mass production with short cultivation time, high yield, and high carbohydrate content in general. However, this method can not produce the effective triterpene compounds. Therefore, the research is restricted to the function of polysaccharide and its potential is limited. Solid cultivation is filling various grains into plastic bag or container as medium for higher yield. It produces some kinds of triterpene with more complete features than that from liquid fermentation. However, the production rate is not stable, and it is hard to separate fungi from its medium. Therefore, the grain medium is usually harvested simultaneously causing less than 5% recovery of *Antrodia cinnamomea*. As a result, total activity is decreasing, and the cultivation time is as long as 3~4 months. Wood cultivation is using *Cinnamomum kanehirae* Hay. to culture *Antrodia cinnamomea*, which is used to solve the stealing problem of *Cinnamomum kanehirae* and *Antrodia cinnamomea* without real benefit. The problems with wood cultivation includes 1~2 years of growth period, limited source of wood, and extreme quality variation between each lot leading to unstable product quality.

In order to improve this situation for massive production of *Antrodia cinnamomea* with high pharmacological activity, the present invention is invented.

Figure 7:
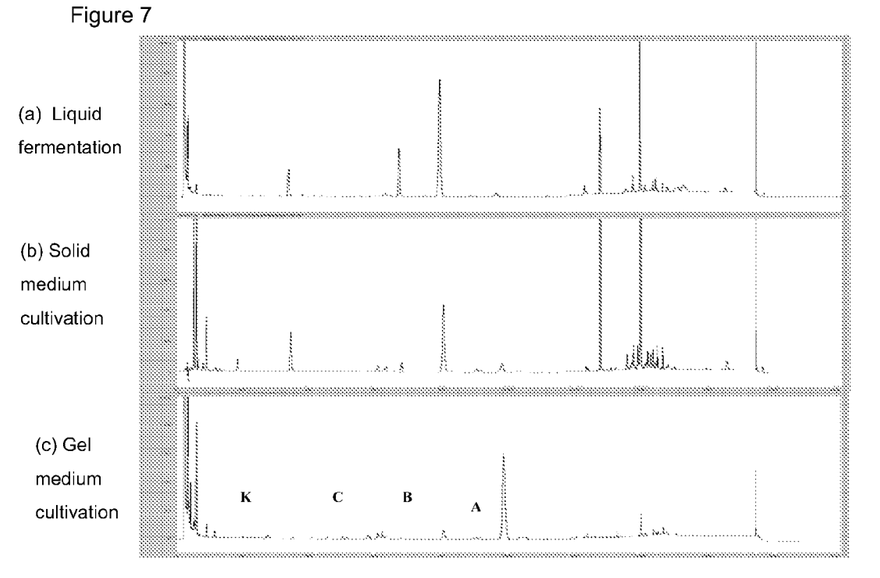
FIG. 7 shows the HPLC chromatogram of *Antrodia cinnamomea* from three different cultivation methods. A: Zhankuic acid A; B: Zhankuic acid B; C: Antcin K.

Therefore, the present invention is related to a gel medium cultivated *Antrodia cinnamomea* mycelium extract which exhibits the HPLC features as shown in FIG. 7(c).

The present invention is also related to a mixture which comprises the extract of the present invention.

In preferred embodiment of the mixture, the extract comprises compound as shown in formula I below:

wherein, $R_1$ is α-OH or =O, $R_2$ is β-OH or H, $R_3$ is β-OH or =O, $R_4$ is α-OH or H, and $R_5$ is H.

The mixture of the present invention inhibits cancer cell growth (such as human liver cancer cell) or exhibits liver protection function (such as inhibiting cell released GOT and GPT, reducing the probability of liver fibrosis or liver cell pathogenesis).

In preferred embodiment of the mixture comprises (a) antcin K, wherein $R_1$ is α-OH, $R_2$ is β-OH, $R_3$ is β-OH, $R_4$ is H, and $R_5$ is H; (b) zhankuic acid A, wherein $R_1$ is O, $R_2$ is H, $R_3$ is =O, $R_4$ is H, and $R_5$ is H; (c) zhankuic acid B, wherein $R_1$ is α-OH, $R_2$ is H, $R_3$ is =O, $R_4$ is H, and $R_5$ is H; or (d) zhankuic acid C, wherein $R_1$ is α-OH, $R_2$ is H, $R_3$ is =O, $R_4$ is α-OH, and $R_5$ is H.

The present invention is also related to a fungal cultivation method, which comprises the following steps:

a) small scale fungal cultivation on medium for fungal propagation;

b) inoculate fungi containing medium onto a gel medium which is suitable for at least two fungal culture blocks;

c) culture gel medium till fungal maturation; and d) harvest fungi from matured fungal medium.

The fungi of the present invention is obtained from wild or artificial cultivated *Antrodia cinnamomea*.

The gel medium of the present invention contains basal material (such as agar), carbon source (such as glucose, fructose, galactose, lactose, starch, cellulose, sucrose or any combination from above), nitrogen source (such as peptone, tripeptone, beef extract, malt extract, yeast extract or any combination from above), extender (such as sunflower oil, olive oil, vitamin B6 or any combination from above), and inorganic salt (such as phosphate, sodium chloride, magnesium sulfate, potassium chloride or any combination from above). Inorganic salt comprises but is not limited to $K_2HPO_3$, $K_3PO_3$, $KH_2PO_3$, $NaH_2PO_3$, $Na_2HPO_3$ or any combination from above.

The weight percentage of each component in the gel medium in the present invention is as below:

The weight percentage of basal material is 0.5~3%.

The weight percentage of carbon source is 0.5~30%.

The weight percentage of nitrogen source is 0.05~5%.

The weight percentage of extender is 0.005~0.05%.

The weight percentage of inorganic salt is 0.01~2.5%.

The gel medium in the present invention is incubated at 16~32C for 20~45 days.

The present invention has been examined by anti-cancer cell growth assay, anti-free radical assay, inhibition of cell released GOT and GPT assay, and in vivo liver protection assay and has demonstrated significant curing effect in above assays.

Features and advantages of the present invention are revealed in the following preferred embodiments and claims.

EXAMPLES

The following examples illustrate the present inventions as material and method guidance but not limited to the same.

Example 1

Cultivation Method

Figure 1:
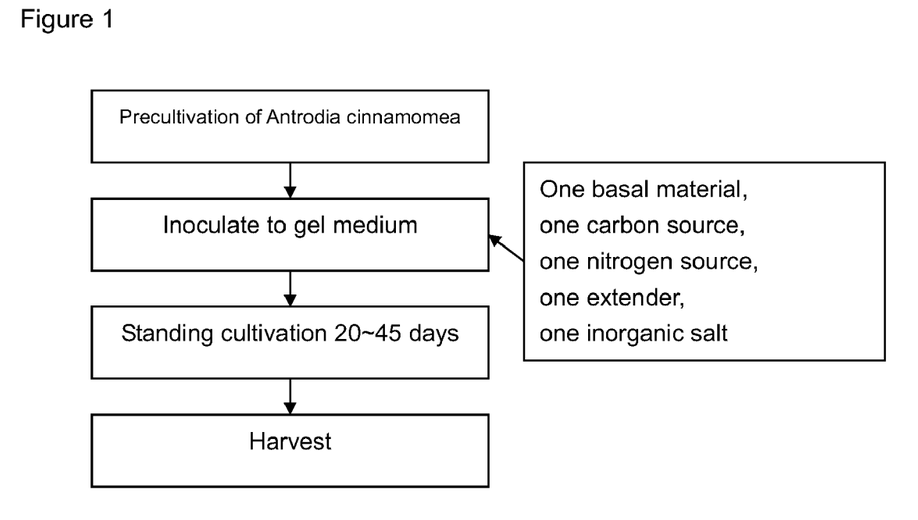
FIG. 1 shows a flow chart of *Antrodia cinnamomea* cultivation method.

FIG. 1 shows a flow chart of *Antrodia cinnamomea* cultivation method in preferred embodiment of the present invention. As shown in FIG. 1, the first step is precultivation of *Antrodia cinnamomea*, such as on a slant medium. In this step, *Antrodia cinnamomea* is obtained wildly or artificially cultivated. The purpose of precultivaiton is to reserve *Antrodia cinnamomea* strain as a source for later artificial cultivation. Precultivation condition and method can be used as any known method.

After that, inoculate *Antrodia cinnamomea* on a gel medium. In other words, take part of the precultivated *Antrodia cinnamomea* and inoculate it on a gel medium for cultivation. The gel medium of the present invention comprises a basal material, a carbon source, a nitrogen source, an extender and an inorganic salt. The weight percentage of basal material such as agar is 0.5~3% relative to the 100% total weight of gel medium.

Besides, carbon source of the gel medium comprises glucose or dextrose, fructose, galactose, lactose, starch, cellulose, sucrose and any combination from above. The weight percentage of carbon source is 0.5~30% relative to the 100% total weight of gel medium.

In addition, nitrogen source of the gel medium comprises peptone, tripeptone, beef extract, malt extract, yeast extract and any combination from above. The weight percentage of nitrogen source is 0.05~5% relative to the 100% total weight of gel medium.

Other than that, extender of the gel medium comprises sunflower oil, olive oil, vitamin B6 and any combination from above. The weight percentage of extender is 0.005~0.05% relative to the 100% total weight of gel medium.

Besides, inorganic salt of the gel medium comprises phosphate, sodium chloride, magnesium sulfate, potassium chloride and any combination from above. The phosphate comprises $K_2HPO_3$, $K_3PO_3$, $KH_2PO_3$, $NaH_2PO_3$, $Na_2HPO_3$ and any combination from above. The weight percentage of inorganic salt is 0.01~2.5% relative to the 100% total weight of gel medium.

Temperature for *Antrodia cinnamomea* cultivation in gel medium is between 16~32° C. The shaking condition for gel medium is standing still. The cultivation time is between 20~45 days.

The cultivated *Antrodia cinnamomea* exhibits the same physiological activity as fruiting body of wild *Antrodia cinnamomea*. Therefore, it can be used for inhibiting human cancer cell growth and lowering GOT and GPT rising from liver damage.

Test results are listed below to demonstrate that cultivated *Antrodia cinnamomea* based on the present invention has the ability to inhibit human cancer cell growth and lower GOT and GPT rising from liver damage.

Example 2

Anti-Human Cancer Cell Growth Assay

This assay is based on anti-cancer drug screen assay developed by National Cancer Institution (NCI). The assay is performed with human cancer cell line (Hep 3B) in vitro. Human cancer cell line (Hep 3B) is cultured in fetal serum medium for 24 hours before replacing it with new medium, and then testing samples are added to culture for 72 hours. MTT assay is used to evaluate cell survival rate. Cultured *Antrodia cinnamomea* obtained based on the present invention is used in human liver cancer cell inhibition assay by calculating the cell survival rate in 96-well microtiter plate and evaluating it with MTT assay.

MTT Assay:

MTT(3-[4,5-Dimethylthialzol-2-yl]-2,5-diphenyltetrazolium bromide) is tetrazolium, a yellow pigment, which can be adsorbed by living cells and reduced to blue formazan by succinate-tetrazolium reductase in mitochondria. It is usually used for screening chemical effect on cell growth and proliferation.

Figure 2:
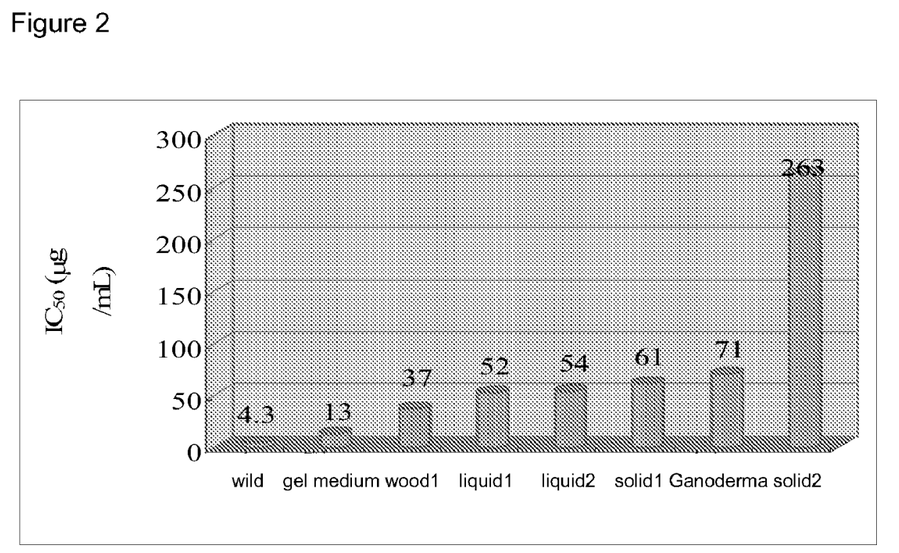
FIG. 2 illustrates a bar graph of inhibition effect of *Antrodia cinnamomea* extracts on human cancer cells.

FIG. 2 shows that gel medium cultured *Antrodia cinnamomea* exhibits higher activity than liquid or solid medium cultured ones on inhibiting human liver cancer cell growth, and its activity is the most similar to that from wild *Antrodia cinnamomea*.

Example 3

Anti-Free Radical Assay

This assay is performed by DPPH clearance ability in vitro. Add DPPH solution into different concentration of *Antrodia cinnamomea* ethanol extract, mix it thoroughly and let it react in the dark for 30 minutes before detecting OD 517 nm with a spectrophotometer. The lower the OD value represents stronger clearing ability.

Figure 3:
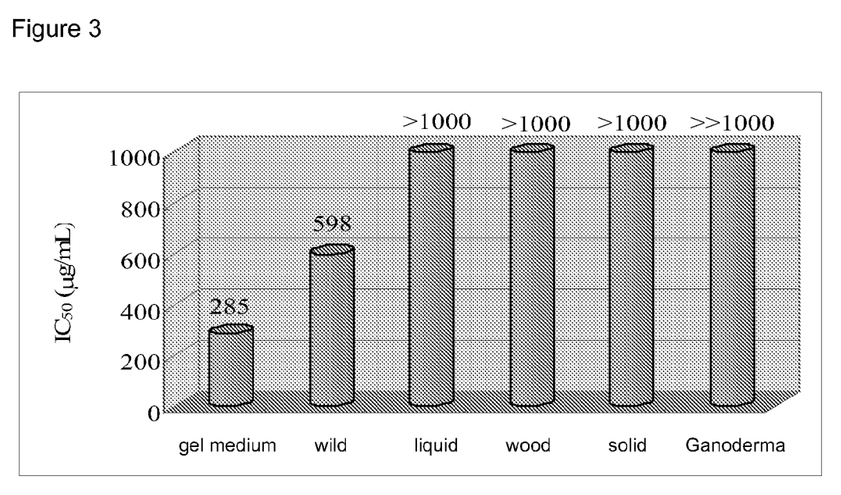
FIG. 3 illustrates a bar graph of scavenging effect of *Antrodia cinnamomea* extracts on DPPH (1,1-diphenyl-2-picrylhydrazyl) radicle.

FIG. 3 shows that gel medium cultured *Antrodia cinnamomea* has higher activity than liquid or solid medium cultured *Antrodia cinnamomea* and wild ones on DPPH clearance ability.

Example 4

Inhibition of Cell Released GOT Assay

This assay is performed with human liver cancer cell line (Hep G2) in vitro. Human liver cancer cell line (Hep G2) is cultured in medium containing fetal bovine serum for 24 hours before replacing it with new medium, and then testing sample and $CCl_4$ are added for 1 hour. Mix supernatant with 4% MTS serum free medium and detect OD 490 nm value by ELISA reader after 40 minutes. This assay is performed with cultured *Antrodia cinnamomea* obtained based on the present invention for inhibition of cell released GOT, and calculated by the OD value in 24-well microtiter plate. Lower OD value represents better inhibition effect.

Figure 4:
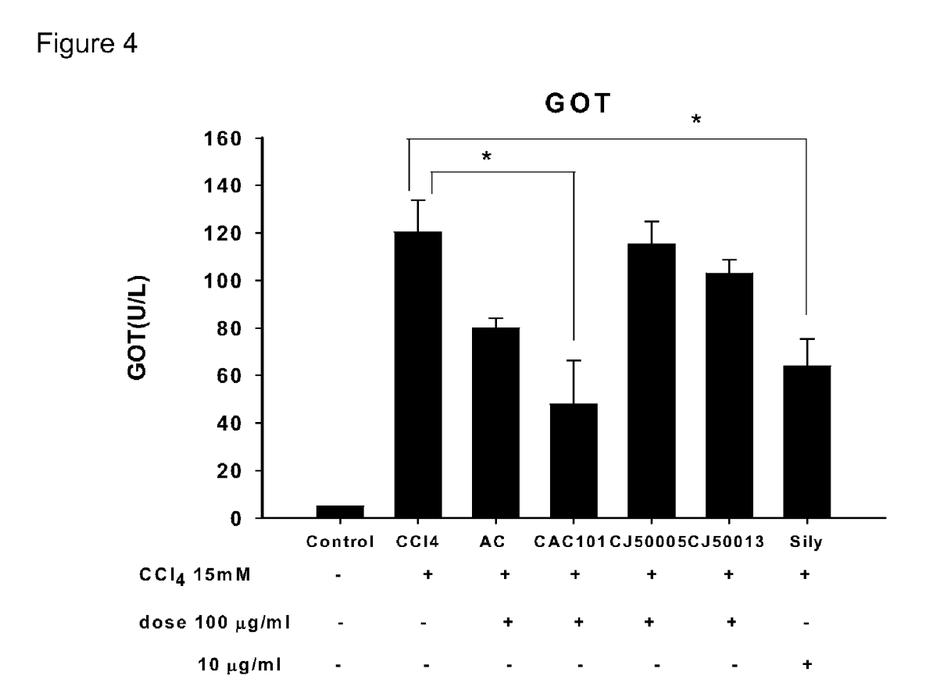
FIG. 4 illustrates the effect of *Antrodia cinnamomea* extracts and $CCl_4$ on cell released GOT.

FIG. 4 shows gel medium cultured *Antrodia cinnamomea* (CAC101) has better inhibition activity on cell release GOT than alternative cultivated *Antrodia cinnamomea* (CJ50005, CT50013) and wild ones (AC).

Example 5

In Vivo Liver Protection Activity Assay

The animal model is performed with $CCl_4$ induced rat chronic liver damage.

Animal model is performed with 12-week-old, 250-300 g weight male WISTAR animal. Domesticated laboratory animals are grouped into 6 groups for orally received and $CCl_4$ induced liver disease before tube feeding and *Antrodia cinnamomea* treatment to test the curing effect on $CCl_4$ induced liver damage as shown in Table 1.

TABLE 1

Treatment of each group

| group | Induced chronic liver damage[1] | Oral feeding |
|---|---|---|
| Group 1 (mock) | Olive oil | Water |
| Group 2 (negative control) | 6% $CCl_4$/olive oil | Water |
| Group 3 (positive control) | 6% $CCl_4$/olive oil | Silymarin[2]/2% CMC |
| Group 4 | 6% $CCl_4$/olive oil | Low dose[3] |
| Group 5 | 6% $CCl_4$/olive oil | Moderate dose[4] |
| Group 6 | 6% $CCl_4$/olive oil | High dose[5] |

[1]twice a week, 2.5 ml/kg each time
[2]200 mg/kg everyday
[3]0.15 g/kg everyday
[4]0.45 g/kg everyday
[5]1.35 g/kg everyday Sacrifice all rats at week 8, and examine GOT and GPT of inferior vena cava blood. Empty the blood, take right liver leaf, sample the same portion of 1×1 cm liver tissue and put it into 10% neutral formalin for pathological section.

Figure 5:
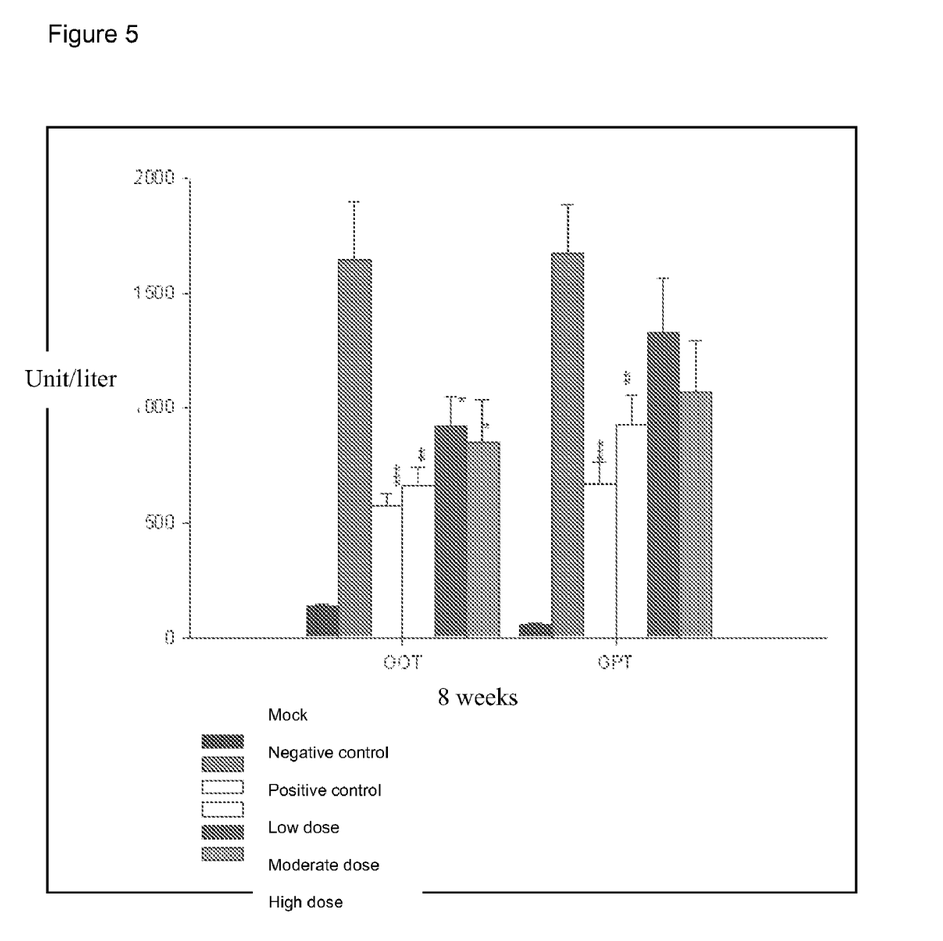
FIG. 5 illustrates *Antrodia cinnamomea* curing effect on $CCl_4$ induced liver damage.
Figure 6:
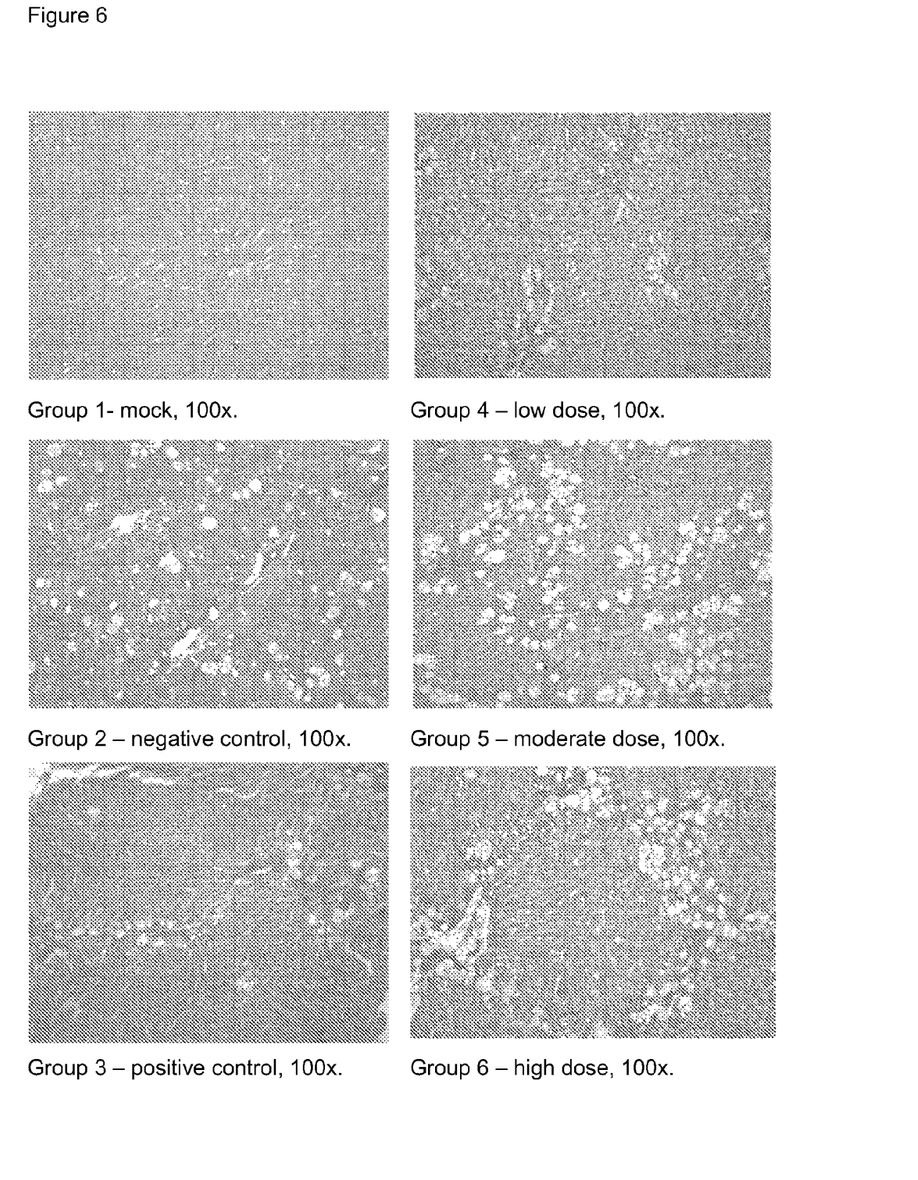
FIG. 6 shows rat liver tissue section of *Antrodia cinnamomea* treated $CCl_4$ induced liver damage.

FIG. 5 demonstrates the curing effect of *Antrodia cinnamomea* on $CCl_4$ induced liver damage. It shows that gel medium cultured *Antrodia cinnamomea* can effectively inhibit $CCl_4$ induced GOT and GPT rising in damaged liver. Liver section is obtained from sacrificed animals. As shown in FIG. 6, group 1 (mock) exhibits normal liver tissue; group 2 (negative control) exhibits extensive liver cell dysplasia and fibrillar connective tissue cutting into liver lobule; group 3 (positive control) shows small amount of liver cell dysplasia and less fibrillar connective tissue cutting into liver lobule; group 4 (low dose) is shown the least liver cell dysplasia; group 5 (moderate dose) is shown extensive liver cell dysplasia and small amount of fibrillar connective tissue cutting into liver lobule; and group 6 (high dose) is shown huge amount of liver dysplasia. It demonstrates that gel medium cultured *Antrodia cinnamomea* obtained based on the present invention can reduce the rising of GOT, GPT, probability of liver fibrosis, and liver cell pathogenesis.

Example 6

*Antrodia cinnamomea* Extract Preparation

*Antrodia cinnamomea* extract is obtained by grinding 100 g of *Antrodia cinnamomea* dry powder, adding 2 L of ethanol, stirring it for 1-4 hours for extraction, filtering the extracted solution for concentration and finally harvesting 15% *Antrodia cinnamomea* extract. Its HPLC chromatogram is shown in FIG. 7. The HPLC column used here is Cosmosil Paked Column 5C18-AR, 4.6×250 mm, and HPLC mobile phase is listed in the table below. The flow rate of HPLC is 1 ml/min, and detector is DAD with wavelength setting at 210, 243, 254, and 280 nm.

| Time (min) | 0.01% $H_3PO_4$ (%) | $CH_3CN$ (%) |
|---|---|---|
| 0 | 70 | 30 |
| 65 | 53 | 47 |
| 110 | 53 | 47 |
| 140 | 0 | 100 |
| 170 | 0 | 100 |
| 175 | 70 | 30 |
| 200 | 70 | 30 |

What is claimed is:

1. A method for producing antcin K, zhankuic acid A, zhankuic acid B or zhankuic acid C from the mycelium of *Antrodia cinnamomea*, which comprises the following steps:
   a) cultivating a fungi wherein the fungi is *Antrodia cinnamomea*, on a medium for fungal propagation;
   b) inoculating the cultivated fungi onto a gel medium;
   c) culturing the fungi-containing gel medium to provide a matured fungal mycelium;
   d) harvesting the matured fungal mycelium; and
   e) isolating the antcin K, zhankuic acid A, zhankuic acid B or zhankuic acid C from the harvested matured fungal mycelium.

2. The method of claim 1, wherein said gel medium comprises a basal material, a carbon source, a nitrogen source, an extender and an inorganic salt.

3. The method of claim 2, wherein said basal material is agar.

4. The method of claim 2, wherein said carbon source comprises glucose, fructose, galactose, lactose, starch, cellulose, sucrose or a combination thereof.

5. The method of claim 2, wherein said nitrogen source comprises peptone, tripeptone, beef extract, malt extract, yeast extract or a combination thereof.

6. The method of claim 2, wherein said inorganic salt comprises phosphate, sodium chloride, magnesium sulfate, potassium chloride or a combination thereof.

7. The method of claim 6, wherein said phosphate comprises $K_2HPO_3$, $K_3PO_3$, $KH_2PO_3$, $NaH_2PO_3$, $Na_2HPO_3$ or a combination thereof.

8. The method of claim 2, wherein weight percentage of said basal material is 0.5-3% by weight of the gel medium.

9. The method of claim 2, wherein weight percentage of said carbon source is 0.5-30% by weight of the gel medium.

10. The method of claim 2, wherein weight percentage of said nitrogen source is 0.05-5% by weight of the gel medium.

11. The method of claim 2, wherein weight percentage of said extender is 0.0005-0.05% by weight of the gel medium.

12. The method of claim 2, wherein weight percentage of said inorganic salt is 0.01-2.5% by weight of the gel medium.

13. The method of claim 2, wherein said gel medium is cultured at 16-32° C. for 20-45 days.

14. The method of claim 2, wherein the extender comprises olive oil, sunflower oil, vitamin $B_6$ or a combination thereof.

* * * * *